(12) United States Patent
Blakey et al.

(10) Patent No.: US 9,682,201 B2
(45) Date of Patent: Jun. 20, 2017

(54) NEGATIVELY BIASED SEALED NEBULIZER SYSTEMS AND METHODS

(71) Applicant: Nektar Therapeutics, San Carlos, CA (US)

(72) Inventors: David Mark Blakey, Hertfordshire (GB); Richard Francis Day, Cambridgeshire (GB)

(73) Assignee: Nektar Therapeutics, San Francisco, CA (US)

( * ) Notice: Subject to any disclaimer, the term of this patent is extended or adjusted under 35 U.S.C. 154(b) by 0 days.

(21) Appl. No.: 14/742,464

(22) Filed: Jun. 17, 2015

(65) Prior Publication Data

US 2015/0283336 A1 Oct. 8, 2015

Related U.S. Application Data

(62) Division of application No. 13/384,575, filed as application No. PCT/US2010/042471 on Jul. 19, 2010, now Pat. No. 9,084,862.

(Continued)

(51) Int. Cl.
*A61M 11/06* (2006.01)
*A61M 15/00* (2006.01)
(Continued)

(52) U.S. Cl.
CPC ......... *A61M 11/007* (2014.02); *A61M 11/003* (2014.02); *A61M 11/005* (2013.01);
(Continued)

(58) Field of Classification Search
CPC .... A61M 11/00; A61M 11/005; A61M 11/06; A61M 15/00; A61M 15/0015;
(Continued)

(56) References Cited

U.S. PATENT DOCUMENTS 3,664,337 A * 5/1972 Lindsey ................. A61M 11/06
128/200.18
4,136,796 A * 1/1979 Dubois .............. B65D 51/1616
220/259.4
(Continued)

FOREIGN PATENT DOCUMENTS

AU 2010/273955 A1 2/2012
AU 2010273955 A1 2/2012
(Continued)

OTHER PUBLICATIONS

Australian Office Action issued Jan. 5, 2015 for Australian Patent application No. AU2010273955 filed on Jul. 19, 2010, all pages.
(Continued)

*Primary Examiner* — Annette Dixon
(74) *Attorney, Agent, or Firm* — Kilpatrick Townsend & Stockton LLP

(57) ABSTRACT

Methods, systems, and devices are described for creating a negative bias pressure within a liquid reservoir. Embodiments may include providing a liquid reservoir coupled with an aerosol generator. The liquid reservoir may be sealed to create the sealed reservoir. An ambient pressure may be maintained while the liquid reservoir is being sealed and the ambient pressure may be maintained in the sealed liquid reservoir until a portion of the liquid is dispensed. Further, embodiments may include vibrating the aperture plate to dispense the portion of the liquid. The portion of the liquid dispensed may decreases the amount of the liquid in the sealed reservoir. By decreasing the amount of liquid in the sealed reservoir, a negative bias pressure between an air side and a liquid side of the aperture plate may be created.

19 Claims, 9 Drawing Sheets

Related U.S. Application Data

(60) Provisional application No. 61/226,567, filed on Jul. 17, 2009.

(51) Int. Cl.
|  |  |
|---|---|
| *A61M 16/14* | (2006.01) |
| *A61M 11/00* | (2006.01) |
| *B05B 17/00* | (2006.01) |
| *A61M 16/00* | (2006.01) |
| *A61M 16/06* | (2006.01) |
| *A61M 16/08* | (2006.01) |
| *A61M 16/20* | (2006.01) |

(52) U.S. Cl.
CPC ........ *A61M 11/06* (2013.01); *A61M 15/0085* (2013.01); *A61M 16/0057* (2013.01); *A61M 16/06* (2013.01); *A61M 16/0875* (2013.01); *A61M 16/14* (2013.01); *A61M 16/208* (2013.01); *B05B 17/0646* (2013.01); *A61M 2205/582* (2013.01)

(58) Field of Classification Search
CPC .......... A61M 15/0018; A61M 15/0021; A61M 15/0065; A61M 15/008; A61M 15/0085; A61M 15/0086; A61M 15/0088; A61M 15/009; A61M 16/00; A61M 16/08; A61M 16/10; A61M 16/125; A61M 16/20; A61M 16/208; A61M 16/209; A61M 2205/123; A61M 2205/3375; A61M 2205/3386; A61M 2205/582; A61M 2209/04; A61M 2209/10
USPC ............ 128/200.11, 200.13, 200.14, 200.16, 128/200.21, 200.22, 200.24, 201.28, 128/203.12, 203.15, 203.16, 203.17, 128/203.19, 203.24, 204.14, 205.24
See application file for complete search history.

(56) References Cited

U.S. PATENT DOCUMENTS

| | | | |
|---|---|---|---|
| 4,484,577 A | 11/1984 | Sackner et al. | |
| 5,161,711 A | 11/1992 | Picozza et al. | |
| 5,164,740 A | 11/1992 | Ivri | |
| 5,515,842 A | 5/1996 | Ramseyer et al. | |
| 5,586,550 A | 12/1996 | Ivri et al. | |
| 5,758,637 A | 6/1998 | Ivri et al. | |
| 5,922,675 A | 7/1999 | Baker et al. | |
| 5,938,117 A | 8/1999 | Ivri | |
| 6,014,970 A | 1/2000 | Ivri et al. | |
| 6,085,740 A | 7/2000 | Ivri et al. | |
| 6,235,177 B1 | 5/2001 | Borland et al. | |
| 6,615,824 B2 | 9/2003 | Power | |
| 6,983,747 B2 * | 1/2006 | Gallem ............. | A61M 15/0085 128/200.14 |
| 7,059,320 B2 * | 6/2006 | Feiner ............... | A61M 15/0085 128/200.16 |
| 7,322,349 B2 | 1/2008 | Power | |
| 8,115,366 B2 | 2/2012 | Hoffman et al. | |
| 8,283,984 B2 | 10/2012 | Lin | |
| 8,616,195 B2 | 12/2013 | Power et al. | |
| 9,084,862 B2 | 7/2015 | Blakey et al. | |
| 2001/0039389 A1 | 11/2001 | Sakurai et al. | |
| 2002/0129813 A1 | 9/2002 | Litherland et al. | |
| 2003/0196660 A1 | 10/2003 | Haveri | |
| 2004/0089295 A1 | 5/2004 | Gallem et al. | |
| 2005/0011514 A1 | 1/2005 | Power et al. | |
| 2005/0034719 A1 | 2/2005 | Feiner et al. | |
| 2005/0224076 A1 | 10/2005 | Pfichner et al. | |
| 2006/0157052 A1 | 7/2006 | Foley et al. | |
| 2006/0213507 A1 | 9/2006 | Foley et al. | |
| 2007/0062520 A1 | 3/2007 | Nobutani et al. | |
| 2008/0006264 A1 | 1/2008 | Gallem et al. | |
| 2009/0288658 A1 | 11/2009 | Charan et al. | |
| 2009/0293868 A1 | 12/2009 | Hetzer et al. | |
| 2012/0118284 A1 | 5/2012 | Blakey et al. | |

FOREIGN PATENT DOCUMENTS

| | | |
|---|---|---|
| CA | 2768379 A1 | 1/2011 |
| CN | 102573967 A | 7/2012 |
| DE | 102005038619 A1 | 2/2007 |
| EA | 201200137 A1 | 8/2012 |
| EP | 2453962 A1 | 5/2012 |
| IL | 217513 | 4/2015 |
| IN | 15/2015 | 4/2015 |
| JP | 2012533366 A | 12/2012 |
| JP | 2016-529076 A | 9/2016 |
| KR | 20120052998 A | 5/2012 |
| MX | 2012000748 A | 4/2012 |
| WO | 2009/063814 A1 | 5/2009 |
| WO | 2011/009131 A1 | 1/2011 |
| WO | 2011/009133 A1 | 1/2011 |

OTHER PUBLICATIONS

Chinese Office Action mailed on Mar. 13, 2013 for Chinese Patent application No. CN201080036582.9 filed on Jul. 19, 2010, all pages.
Chinese Office Action issued Sep. 22, 2013 for Chinese Patent application No. CN201080036582.9 filed on Jul. 19, 2010, all pages. [Not Translated].
Eurasian Office Action mailed on Jan. 17, 2014 for Eurasian Patent application No. EA201200137 filed on Jul. 19, 2010, all pages.
Eurasian Office Action mailed on Sep. 23, 2014 for Eurasian Patent Application No. EA201200137 filed on Jul. 19, 2010, all pages.
Eurasian Office Action mailed on May 21, 2015 for Eurasian Patent Application No. EA201200137 filed on Jul. 19, 2010, all pages.
European Search Report completed on Aug. 13, 2014 for European Application No. EP10800671 filed on Jul. 19, 2010, all pages.
Israeli Office Action dated Aug. 8, 2013 for Israeli Patent Application No. IL217513 filed on Jul. 19, 2010, all pages. [Not Translated].
International Search Report and Written Opinion mailed on Sep. 2, 2010 for International Patent Application No. PCT/US2010/042471 filed on Jul. 19, 2010, all pages.
International Preliminary Report on Patentability issued on Jan. 17, 2012 for International Patent Application No. PCT/US2010/042471 filed on Jul. 19, 2010, all pages.
Japanese Office Action mailed on Jul. 29, 2014 for Japanese Patent Application No. JP2012520837 filed on Jul. 19, 2010, all pages.
Japanese Office Action issued on Apr. 21, 2015 for Japanese Patent Application No. JP2012520837 filed on Jul. 19, 2010, all pages. [Not Translated].
Mexican Office Action dated on Jul. 1, 2014 for Mexican Patent Application No. MX/a/2012/000748 filed on Jul. 19, 2010, all pages. [Not Translated].
Mexican Office Action issued Dec. 2, 2014 for Mexican Patent application No. MX/a/2012/000748 filed on Jul. 19, 2010, all pages. [Not Translated].
Mexican Office Action issued Apr. 9, 2015 for Mexican Patent application No. MX/a/2012/000748 filed on Jul. 19, 2010, all pages. [Not Translated].
European Patent Application No. 10800671.9 filed Jul. 19, 2010, Office Action mailed Mar. 18, 2016, all pages.
Office Action mailed Aug. 4, 2016 for Korean Application No. 10-2012-7004280, filed Jul. 19, 2010; all pages.
Office Action mailed May 30, 2016 for Canada Application No. 2,768,379, filed Jul. 29, 2010; all pages.
International Search Report and Written Opinion mailed Jul. 7, 2014 for International Patent Application No. PCT/US2013/058004.

* cited by examiner

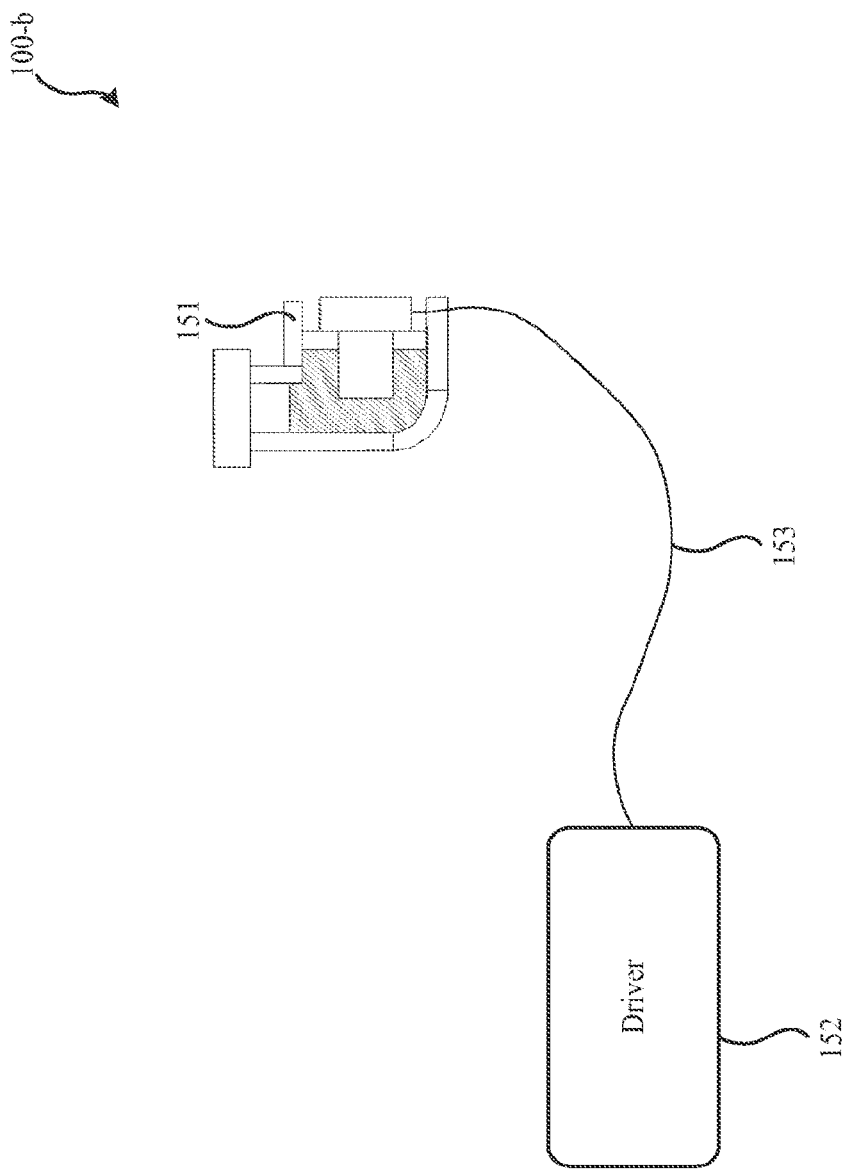

```
          ┌─────────────────────────────┐
  710 ────┤ Receiving liquid drug in the│
          │       drug reservoir         │
          └──────────────┬──────────────┘
                         ▼
          ┌─────────────────────────────┐
  720 ────┤   Storing the liquid drug in │
          │       the drug reservoir     │
          └──────────────┬──────────────┘
                         ▼
          ┌─────────────────────────────┐
  730 ────┤   Sealing the drug reservoir to│
          │    prevent air from entering │
          └──────────────┬──────────────┘
                         ▼
          ┌─────────────────────────────────┐
  740 ────┤ Discharging liquid drug from the │
          │ drug reservoir to an aerosol generator│
          └──────────────┬──────────────────┘
                         ▼
          ┌─────────────────────────────┐
  750 ────┤     Aerosolizing liquid      │
          │             drug             │
          └──────────────┬──────────────┘
                         ▼
          ┌─────────────────────────────┐
  760 ────┤   Creating a negative bias   │
          │ pressure in the drug reservoir│
          └─────────────────────────────┘
```

FIG. 7

- 810 — Receiving liquid drug in the drug reservoir
- 820 — Storing the liquid drug in the drug reservoir
- 830 — Sealing the drug reservoir to prevent air from entering
- 840 — Discharging liquid drug from the drug reservoir to an aerosol generator
- 845 — Receiving a control signal from a driver unit
- 850 — Aerosolizing liquid drug
- 860 — Creating a negative bias pressure in the drug reservoir
- 865 — Additional liquid drug to be added to drug reservoir?
  - Yes → 875 Remove drug reservoir cap → 880 Receive additional liquid drug in drug reservoir → 890 Store additional liquid drug in drug reservoir → (back to 830)
  - No → 870 End

FIG. 8

NEGATIVELY BIASED SEALED NEBULIZER SYSTEMS AND METHODS

CROSS-REFERENCES TO RELATED APPLICATIONS

This application is a divisional of U.S. patent application Ser. No. 13/384,575, filed Jan. 17, 2012, entitled "NEGATIVELY BIASED SEALED NEBULIZERS SYSTEMS AND METHODS," which is a U.S. National Phase of PCT/US2010/042471 filed on Jul. 19, 2010, entitled "NEGATIVELY BIASED SEALED NEBULIZERS SYSTEMS AND METHODS," which claims the benefit of U.S. Provisional Patent Application No. 61/226,567, filed Jul. 17, 2009 entitled "NEGATIVELY BIASED SEALED NEBULIZERS SYSTEMS AND METHODS," and is related to Provisional Patent Application No. 61/226,591, filed Jul. 17, 2009 entitled "SYSTEMS AND METHODS FOR DRIVING SEALED NEBULIZERS," the entire disclosures of which is incorporated by reference for all purposes.

BACKGROUND OF THE INVENTION

Embodiments of the present invention relate to nebulizers. In particular, the present invention relates to use of a nebulizer with a sealed drug reservoir to build up and maintain an internal negative bias pressure.

A wide variety of procedures have been proposed to deliver a drug to a patient. In some drug delivery procedures the drug is a liquid and is dispensed in the form of fine liquid droplets for inhalation by a patient. A patient may inhale the drug for absorption through lung tissue. Further, the droplets forming the mist may need to be very small to travel through small airways of the patient's lungs, and consistent in size to assure proper absorption. Such a mist may be formed by a nebulizer.

SUMMARY

Creating a negative bias pressure on the liquid side of an aperture used for aerosolizing liquid drug may allow for more efficient and consistent delivery of aerosolized liquid drugs to a patient. Such a negative bias may be created by reducing the pressure within the drug reservoir of a nebulizer. This may be accomplished by sealing the drug reservoir then discharging an amount of liquid drug from the reservoir. Because neither air, nor anything else, is able to fill the space vacated by the discharged liquid drug, the pressure within the drug reservoir decreases, thereby creating a negative bias pressure within the liquid drug reservoir and on the liquid side of the aperture aerosolizing the liquid drug.

In some embodiments, a method for creating a negative bias pressure within a sealed reservoir may be present. The method may include providing a liquid reservoir coupled with an aerosol generator, the aerosol generator comprising an aperture plate, the aperture plate having a liquid side and an air side. The method may also include receiving a liquid in the liquid reservoir. The method may include sealing the liquid reservoir to create the sealed reservoir. An ambient pressure may be maintained while the liquid reservoir is being sealed. The ambient pressure may be maintained in the sealed liquid reservoir until a portion of the liquid is dispensed. The method may include vibrating the aperture plate to dispense liquid. Dispensing liquid may decrease the amount of liquid in the sealed reservoir. The method may include decreasing the amount of liquid in the sealed reservoir to create a negative bias pressure between an air side and a liquid side of the aperture plate.

In some embodiments, a cap is provided, wherein the cap comprises a first portion configured to couple with the liquid reservoir and a second portion configured to screw into the first portion of the cap. The method may further comprise screwing the second portion of the cap into the first portion of the cap, wherein a passageway allows the ambient pressure to be maintained in the liquid reservoir as the second portion of the cap is screwed into the first portion of the cap. In some embodiments, a cap is provided, wherein the cap comprises a flexible seal and a pivot. The method may include pivoting the cap against the liquid reservoir, such that the flexible seal seals the liquid reservoir. In some embodiments, a cap is provided that comprises a one-way valve and a seal. The method may further include pressing the cap onto the liquid reservoir such that the seal couples the cap with the liquid reservoir, wherein the one-way valve the ambient pressure to be maintained as the liquid reservoir is sealed. In some embodiments, the cap is shaped to reduce headspace within the liquid reservoir. In some embodiments, a cap is provided that comprises a plunger and a stopper. The method may further include placing the cap on the liquid reservoir such that the cap covers the liquid reservoir, wherein the ambient pressure is maintained by a passageway between the cap and the stopper. The method may further comprise pulling the plunger of the cap, wherein the plunger seals the liquid reservoir by moving the stopper to obstruct the passageway between the stopper and the cap.

In some embodiments, sealing the liquid reservoir to create the sealed reservoir uses a reservoir cap. The method may further comprise, releasing, via the reservoir cap, air as the liquid reservoir is sealed to create the sealed reservoir. The method may further comprise unsealing the liquid reservoir using a reservoir cap; placing additional liquid in the liquid reservoir; and resealing the liquid reservoir using the reservoir cap. Also, the method may comprise receiving, by the aerosol generator, a control signal from a driver unit. The control signal from the driver unit may be used to vibrate the aperture plate to dispense liquid. The liquid may be a drug and the liquid reservoir may be a liquid drug reservoir.

In some embodiments, a system for creating a negative bias pressure within a liquid reservoir is present. The system may include an aerosol generator comprising an aperture plate having a liquid side and an air side, wherein the aerosol plate is configured to be vibrated to dispense liquid. The liquid reservoir may be configured to: receive liquid; store liquid; discharge liquid to the aerosol generator; and seal, such that a negative bias pressure develops between the liquid side and the air side of the aperture plate as liquid is discharged from the liquid reservoir. The system may include a cap configured to maintain an ambient pressure while the liquid reservoir is being sealed. The ambient pressure may be maintained in the sealed liquid reservoir until a portion of the liquid is dispensed.

In some embodiments, a system for creating a negative bias pressure on liquid to be aerosolized is present. The system may include means for receiving liquid; means for storing liquid; means for sealing the stored liquid in a sealed environment; means for maintaining an ambient pressure on the stored liquid while the stored liquid is being sealed; means for maintaining the ambient pressure in the sealed environment until a portion of the liquid is dispensed; means for discharging liquid of the stored liquid to be aerosolized; means for aerosolizing liquid of the discharged liquid; and means for allowing a negative bias pressure to develop on the stored liquid and discharged liquid.

BRIEF DESCRIPTION OF THE DRAWINGS

A further understanding of the nature and advantages of the present invention may be realized by reference to the following drawings. In the appended figures, similar components or features may have the same reference label. Further, various components of the same type may be distinguished by following the reference label by a second label that distinguishes among the similar components. If only the first reference label is used in the specification, the description is applicable to any one of the similar components having the same first reference label irrespective of the second reference label.

FIG. 1B illustrates a simplified embodiment of a nebulizer with a driver unit.

FIG. 7 illustrates a method for creating a negative bias pressure in a drug reservoir.

FIG. 8 illustrates a method for creating a negative bias pressure in a drug reservoir, adding additional liquid drug, and then resealing the drug reservoir.

DETAILED DESCRIPTION OF THE INVENTION

Figure 1A:
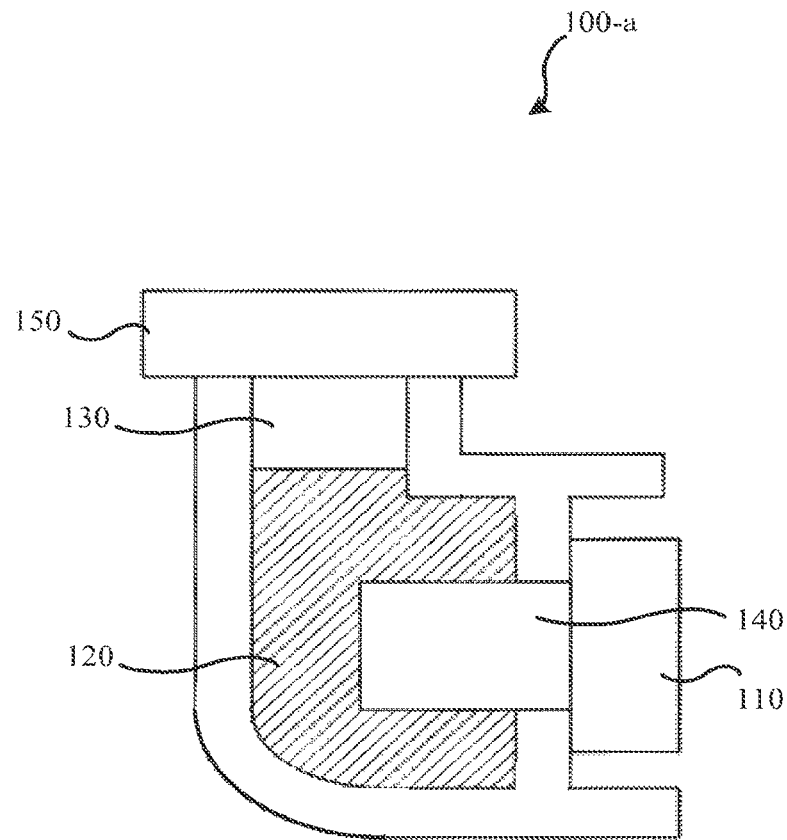
FIG. 1A illustrates a simplified embodiment of a nebulizer.

Devices, systems, and methods are described for the implementation of a novel architecture of nebulizers. The invention provides various ways of improving the efficiency and consistency of a liquid mist ejected from the vibrating aperture plate of a nebulizer. In some nebulizers, also known as aerosol generators, operating conditions, such as the existence of excess liquid on the air-side (front face) of the vibrating aperture plate of the nebulizer, may change over time. Such excess liquid may arise from over pressure of the liquid reservoir, forcing some liquid to leak through the aperture. Also, during operation of the nebulizer, certain features of the droplet ejection process may lead to stray droplets falling back onto the aperture plate. This excess liquid may adversely affect the ejection efficiency of the nebulizer, which is directly related to the flow rate and droplet diameter properties of the liquid mist ejected from the nebulizer.

In addition, such excess liquid on the air-side of the aperture plate may lead to the ejection of larger diameter droplets from the vibrating aperture. These larger droplet diameters may result in an improper amount of the drug being administered to the patient and the drug being deposited in the large airways of the patient's lungs as opposed to the smaller passageways where the drug may be absorbed more readily. When the pressure on the reservoir side of the aperture plate, which may be connected to the drug reservoir of the nebulizer, is lower than the air-pressure immediately on the air-side of the aperture plate what is known as a "negative bias pressure" may be created. Such a negative bias pressure may cause the efficiency of the nebulizer to be increased, thus allowing it to achieve higher liquid flow rates, with smaller and more consistent droplet size, than in comparable conditions without a bias pressure. The negative bias pressure may be created by sealing the drug reservoir. As the liquid drug is drained from the drug reservoir (with little or no air entering to replace the dispensed liquid drug's volume), a negative bias pressure may be created.

FIG. 1 illustrates an embodiment of a possible nebulizer 100. The nebulizer 100 may include a nebulizer element 110 (which is alternatively referred to as an aperture plate), a drug reservoir 120, a head space 130, an interface 140, and a cap 150. The nebulizer element 110 may be comprised of a piezoelectric ring that may expand and contract when an electric voltage is applied to the ring. The piezoelectric ring may be attached to a perforated membrane. Such a perforated membrane may have a number of holes passing through it. When an electric voltage is applied to the piezoelectric ring, this may cause the membrane to move and/or flex. Such movement of the membrane while in contact with a liquid may cause the atomization of the liquid, generating a mist of liquid droplets.

Embodiments of nebulizer 100 may utilize a piezoelectric ring to vibrate a perforated membrane. Further, other nebulizers, and the techniques associated with such nebulizers, are described generally in U.S. Pat. Nos. 5,164,740; 5,938,117; 5,586,550; 5,758,637, 6,014,970, 6,085,740; 6,235,177; 6,615,824, 7,322,349 the complete disclosure of which are incorporated by reference for all purposes.

A supply of a liquid, commonly a liquid drug, may be held in the drug reservoir 120 (also referred to as a liquid reservoir). As illustrated, a drug reservoir is partially filled with the liquid drug. As the liquid drug is atomized, the amount remaining in the drug reservoir 120 may decrease. Depending on the amount of liquid drug in the drug reservoir 120, only a portion of the reservoir may be filled with liquid drug. The remaining portion of the drug reservoir 120 may be filled with gas, such as air. This space is commonly referred to as head space 130 and dead volume. An interface 140 may serve to transfer minute amounts of liquid drug between the drug reservoir 120 and the nebulizer element 110.

The nebulizer 100-*a* may have a cap 150 sealing the drug reservoir. Such a cap 150 may prevent air from entering the drug reservoir 120. Cap 150 may be attached and sealed to the drug reservoir 120 such that the ambient pressure (e.g., the pressure outside of the drug reservoir 120) is maintained in the drug reservoir 120 until liquid is drained from the drug reservoir 120. Therefore, as the liquid drug is evacuated from the drug reservoir 120, a negative bias pressure may appear in the drug reservoir 120 (i.e. a lower pressure in the drug reservoir than the atmospheric pressure). While the drug reservoir 120 is sealed, air may still enter the drug reservoir 120 through the nebulizer element 110. The greater the difference in pressure between the external environment and the drug reservoir 120, the greater the rate air may enter the drug reservoir 120 through the nebulizer element 110. At a certain difference in pressure between the inside of the drug reservoir 120 and the external environment, the plateau pressure of the nebulizer 100 will be reached. At this point, air external to the nebulizer 100 may enter the drug reservoir 120 through openings in the nebulizer element 110 (also referred to as the "aperture plate") at the same rate that liquid is being atomized by the nebulizer element 110. At the plateau point, air entering the reservoir 120 via nebulizer element 110 may serve to reduce the negative bias pressure or cause it to stabilize and stay roughly at a certain pressure negative bias pressure.

A nebulizer with a sealed drug reservoir may be part of a larger system. The embodiment of FIG. 1B illustrates such a system 100-b. FIG. 1B illustrates a nebulizer 151 with a capped drug reservoir connected to a driver unit 152. The nebulizer with a cap illustrated in FIG. 1B may be the nebulizer with a cap of FIG. 1A, or may represent some other nebulizer. The driver unit 152 may control the rate and size of vibration of the nebulizer element on the nebulizer 151. The driver unit 152 may be connected to the nebulizer element 151 via cable 153. The driver unit may be the driver unit described in co-pending provisional application No. 61/226,591 entitled SYSTEMS AND METHODS FOR DRIVING SEALED NEBULIZERS filed on Jul. 17, 2009, the entire disclosure of which is incorporated by reference for all purposes. Such a driver unit 152 may regulate the voltage and frequency of the signal provided to the nebulizer element of nebulizer 151. The regulation of the voltage and frequency of the signal may be based on the resonance frequency of the nebulizer element of nebulizer 151. Such a signal may vary depending on the magnitude of the negative bias pressure.

Figure 1C:
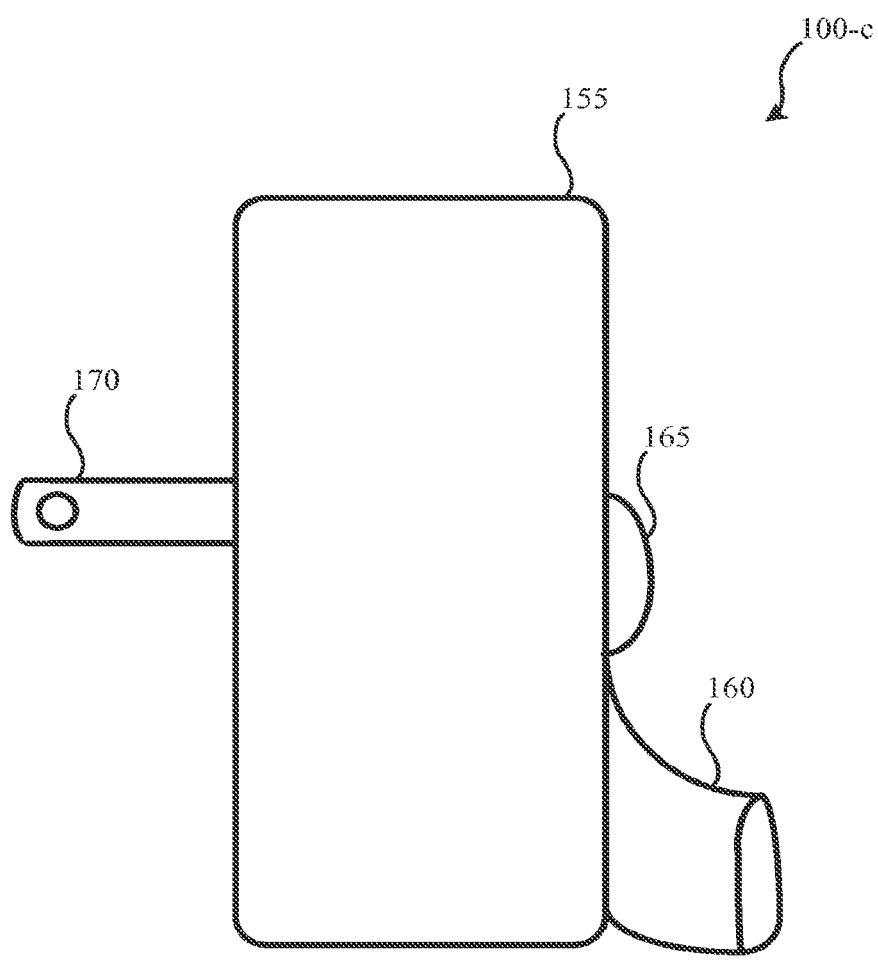
FIG. 1C illustrates a simplified embodiment of a handheld nebulizer with an integrated driver unit.
Figure 1D:
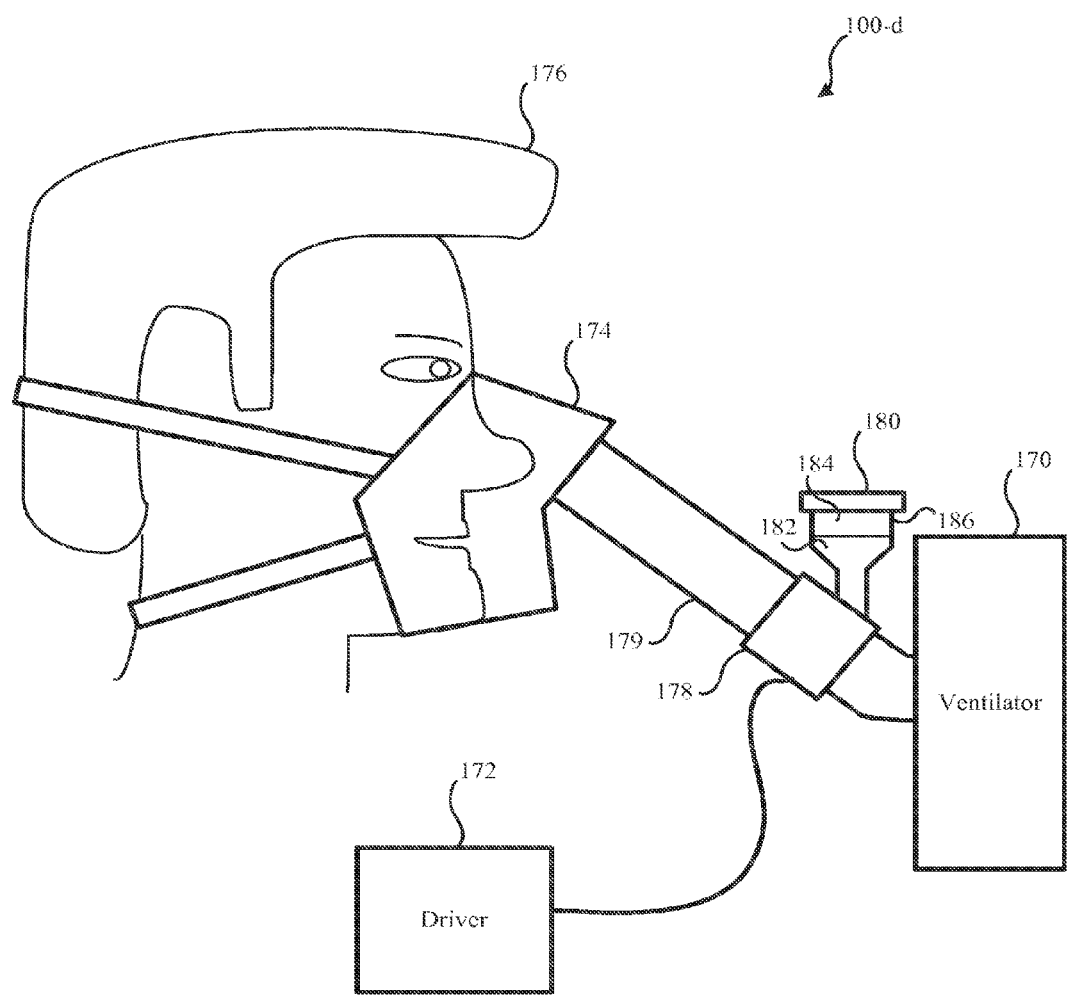
FIG. 1D illustrates a nebulizer integrated with a ventilator.
Figure 2:
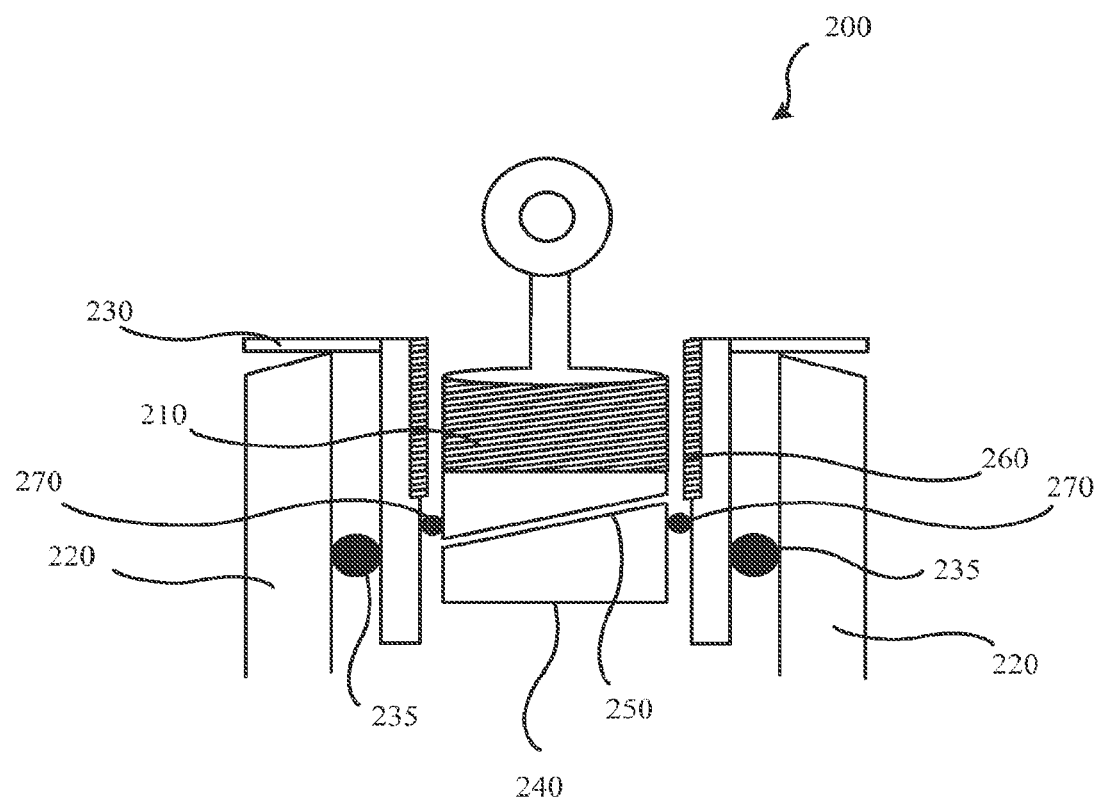
FIG. 2 illustrates a simplified embodiment of a cap that may seal a drug reservoir.
Figure 3:
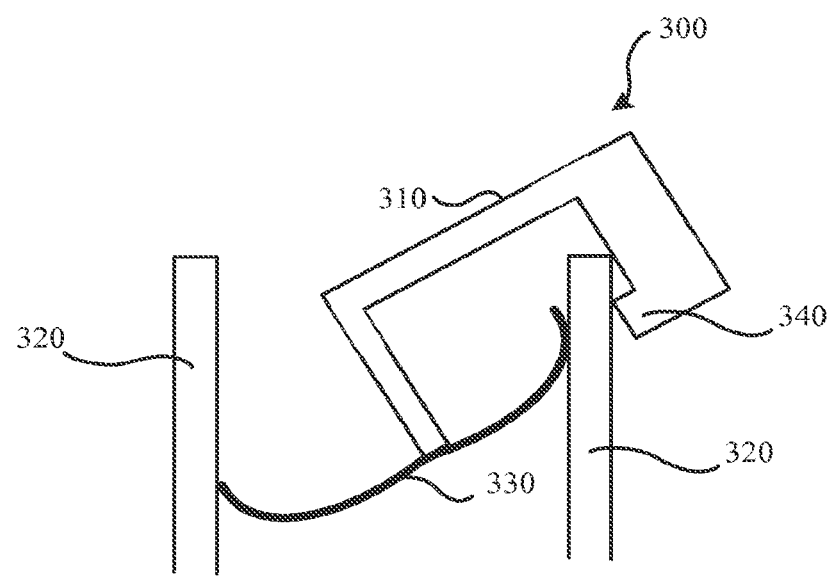
FIG. 3 illustrates another simplified embodiment of a cap that may seal a drug reservoir.
Figure 4:
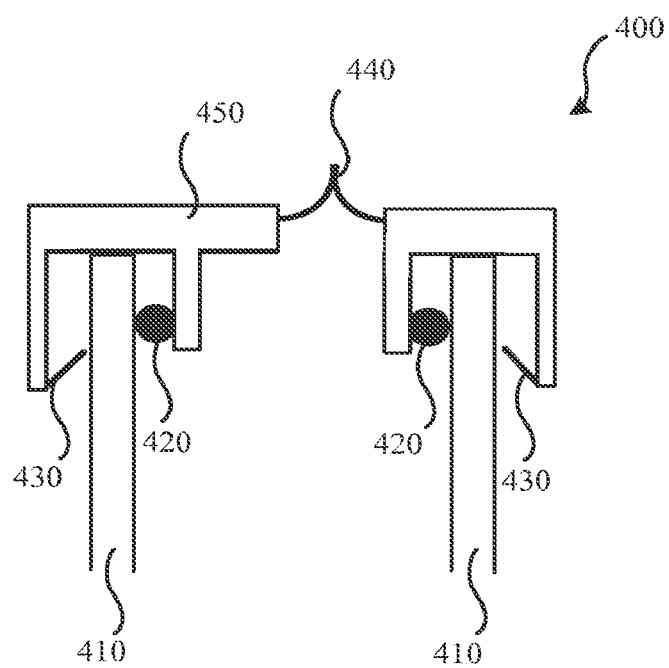
FIG. 4 illustrates yet another simplified embodiment of a cap that may seal a drug reservoir.

In some other embodiments of nebulizers, the driver unit may be incorporated into a handheld unit. Nebulizer 100-c of FIG. 1C illustrates an embodiment of a handheld nebulizer with an integrated driver. Nebulizer 100-c may include a case 155, a mouthpiece 160, and trigger button 165, and an electrical plug 170. Case 155 may contain some or all of the elements found in other embodiments of nebulizers (such as nebulizer 100-a of FIG. 1A) and drivers (such as driver unit 152 of FIG. 1B). Therefore, contained with case 155 may be a sealed drug reservoir and/or a device capable of generating an electrical signal at a particular voltage and frequency to vibrate an aperture plate that aerosolizes liquid stored in the drug reservoir. A person receiving the aerosolized liquid drug may place her mouth on mouthpiece 160 and breath in. While the person receiving the aerosolized liquid drug is breathing in, she may press trigger button 165 to trigger the aperture plate to begin aerosolizing liquid. In some embodiments, nebulizer 100-c may contain a sensor that detects when the person is breathing in and triggers the aperture plate to vibrate without trigger button 165 being necessary.

Nebulizer 100-c may also include an electrical plug 170. Electrical plug 170 may be connected to an electrical outlet to power nebulizer 100-c. Nebulizer 100-c may contain a battery, thereby allowing electrical plug 170 to be connected to an electrical outlet when nebulizer 100-c is not in use by a person to charge the battery. Alternatively, in some embodiments of nebulizer 100-c, electrical plug 170 may need to be connected to an electrical outlet while nebulizer 100-c is in use by a person. In some embodiments, nebulizer 100-c may use replaceable batteries as its power source.

In some embodiments, a nebulizer may operate in conjunction with a ventilator. System 100-d illustrates a nebulizer 178 that supplies aerosolized liquid to a person 176 via a ventilator 170. Ventilator 170 may supply air suitable for breathing to person 176. Ventilator 170 may assist person 176 in breathing by forcing air into the lungs of person 176 and then releasing air to mimic breathing. While person 176 is using ventilator 170, it may be necessary to provide person 176 with aerosolized liquid, such as a liquid drug.

Nebulizer 178 may be connected to a drug reservoir 186 that is sealed by a cap 180. Drug reservoir 186 may contain an amount of liquid drug 182. This liquid drug may be delivered to nebulizer 178 as liquid drug is aerosolized by nebulizer 178. As liquid drug is aerosolized, liquid drug 182 may drain from drug reservoir 186, thereby increasing the volume of headspace 184. Headspace 184 may contain air. Headspace 184 may increase in volume, but also decrease in pressure as liquid drug 182 drains because liquid reservoir 186 is airtight.

Driver 172, which may represent the same driver as driver unit 152 of FIG. 1B (or may represent some other driver unit) may deliver a signal to nebulizer 178. This signal may control an aperture plate of nebulizer 178. Nebulizer 178 may be attached to a tube 179 used to deliver the air and liquid drug to patient 176. Tube 179 may terminate in a mask 174 covering the mouth and/or nose of person 176. The air and aerosolized liquid drug may then enter the airways of person 176.

Nebulizers of FIGS. 1A-1D may create a negative bias pressure with a sealed drug reservoir. The overarching principle behind the bias in pressure formed in the drug reservoir of the nebulizers by the evacuated liquid drug may be described by the ideal gas equation:

$$pV = \text{constant} \quad \text{Eq. 1}$$

In equation 1, p represents pressure and V represents volume. Accordingly, in a sealed drug reservoir, the pressure $p_1$ multiplied by the volume $V_1$ prior to the evacuation of an amount of the liquid drug may equal the pressure $p_2$ multiplied by the volume $V_2$ after the evacuation of the amount of the liquid drug. Therefore, the relationship may be expressed as:

$$p_1 V_1 = p_2 V_2 \quad \text{Eq. 2}$$

$$\therefore p_2 = \frac{p_1 V_1}{V_2}$$

Further, the volume after the liquid drug has been evacuated may be the same as the volume prior to the drug being evacuated plus the change in air volume DV due to the out-flow of the liquid drug from the drug reservoir. From this, a simplified equation may be used to represent the pressure inside the reservoir 120 following evacuation of an amount of the liquid drug:

$$p_2 = \frac{p_1 V_1}{V_1 + DV} \quad \text{Eq. 3}$$

Therefore, to minimize $p_2$, $V_1$ may be minimized. This may be accomplished by minimizing the initial amount of air space (also referred to as "head space") in the drug reservoir, such as head space 184 of FIG. 1D or head space 130 of FIG. 1A.

By way of example only, a drug reservoir may be 9.5 mL. Of this 9.5 mL, 3.6 mL may be filled with a liquid drug, such as Amikacin. Therefore, an initial head space of 5.9 mL is present. To decrease the initial head space while still beginning with the same amount of liquid drug, the size of the drug reservoir may be reduced.

Referring to FIG. 1A, as liquid drug is evacuated from the drug reservoir 120, the negative bias pressure may increase (in other words, the pressure inside the drug reservoir 120 may become lower than the external atmospheric pressure). The bubble point of a stationary aperture plate may be expressed by the following equation:

$$P_b = \frac{2\sigma}{r} \qquad \text{Eq. 4}$$

Here, $P_b$ refers to the bias pressure, σ refers to surface tension of the liquid drug, and r refers to the radius of the holes in the membrane on the vibrating aperture plate. By way of example only, if σ is 0.05, such as for the liquid drug Amikacin, and the radius of the holes in the aperture plate is 2.25 microns, the bias pressure at which air will begin to "bubble" into the drug reservoir is 444 mbar bias pressure. By way of example only, using the liquid drug Amikacin, where the initial head space in the drug reservoir is 1.9 mL, this bubble point may be reached when 2.4 mL of the initial 3.6 mL of the liquid drug has been evacuated from the drug reservoir 120. The bubble point may be greater than or equal to the plateau pressure where the air entering the aperture plate balances the liquid being ejected from the aperture plate.

While the above example refers to the use of the liquid drug Amikacin, other liquid drugs or other liquids may also be used. Further, if a different liquid is used, the value of a may change based on the surface tension of the particular liquid used.

To allow the negative bias pressure to exist within the drug reservoir of the nebulizer, the drug reservoir 120 must be sealed to prevent air from entering the drug reservoir 120 beside through the perforated membrane of the nebulizer element 110. Further, it may be desirable that the drug reservoir 120 of the nebulizer 100 not be permanently sealed. A nebulizer with a resealable drug reservoir 120 may allow for the drug reservoir 120 to be reused or accessed, such as to add an additional amount of liquid drug. As such, the drug reservoir may be either permanently or temporarily capped to prevent air from filling the space created by the evacuated liquid drug. Also, a decrease in the initial dead volume may be desired to minimize V1 as previously described. Therefore, a cap 150 for a drug reservoir of a nebulizer may serve multiple purposes: to seal the drug reservoir from the external environment and to fill at least a portion of the dead volume.

FIG. 2 illustrates an embodiment of a cap to seal a drug reservoir of a nebulizer 200. The nebulizer of FIG. 2 may be any of the nebulizers of FIGS. 1A-1D, or it may be some other nebulizer. A cap 230 may be made of a rigid or semi-rigid material capable of maintaining a seal, such as plastic or metal. In such an embodiment, the cap 230 may be inserted a distance into the drug reservoir 220. Such an insertion may minimize the head space in the drug reservoir 220 of the nebulizer. The greater the distance the cap 230 is inserted into the drug reservoir 220, the greater the amount of head space that may be removed (thereby reducing $V_1$, as previously detailed). In the embodiment of FIG. 2, the cap 230 utilizes o-rings 235 to maintain a seal against the inner edge of the drug reservoir 220. The cap 230 may contain a screw down insert 210. The screw down insert 210 may have threads to allow screw down insert 210 to be screwed into threads 260 of an outer portion of the cap 230. The cap 230 may also use o-rings 270 to maintain a seal against the screw down insert 210. As the screw down insert 210 is screwed into the outer portion of the cap 230, the head space within the drug reservoir 220 may be reduced by a mass of material 240 being inserted into the head space. The farther the screw down insert 210 is screwed down, the farther the mass of material 240 may be inserted into the drug reservoir 220. The screw down insert 210 may be limited from being screwed too far into the drug reservoir 220 by a block at the end of the threads 260 or the threads on screw down insert 210.

When a drug reservoir of a nebulizer is partially filled with liquid drug and a cap is installed on the drug reservoir, the attachment of the cap may compress air within the head space of the drug reservoir, resulting in a positive bias pressure within the drug reservoir. Such a positive bias pressure may cause liquid drug to be forced out of the perforated membrane of the nebulizer. It may be desired that this phenomenon be minimized. In the embodiment of FIG. 2, the screw down insert 210 and/or the mass of material 240 may contain a passageway 250 to maintain the ambient pressure upon insertion of the cap 230. The passageway 250 may allow air to exit the cavity of the drug reservoir 220 as the cap 230 is inserted and the screw down insert 210 is screwed down. The passageway 250 may allow air to pass to outside of o-ring 270. Once the screw down insert 210 is screwed down far enough, the entire passageway 250 may be below the o-ring 270, creating an airtight seal between the cap 230 and the drug reservoir 220.

The screw down insert 210 may later be unscrewed. Unscrewing the screw down insert 210 may leave the mass of material 240 in place, maintaining the air tight seal between the cap 230 and drug reservoir 220 of the nebulizer. Alternatively, unscrewing screw down insert 210 may remove mass of material 240. This may unseal drug reservoir 220, allowing liquid drug to be removed and/or added to drug reservoir 220. The screw down insert 210 may then be used again to reseal drug reservoir 220.

It may also be desired to invert the filled and sealed nebulizer so the air inside the reservoir moves to be adjacent to the aperture plate. The air may then exit through the holes in the aperture plate. This action may reduce the positive pressurization in the nebulizer, and affect the performance of the nebulizer.

FIG. 3 illustrates another embodiment 300 of a cap for a drug reservoir of a nebulizer, such as the nebulizers of FIGS. 1A-1D, or some other nebulizer. The embodiment of FIG. 3 utilizes a pivot-based design. The cap 310 may be inserted at an angle into the cavity of the drug reservoir 320. A seal 330 attached to the cap 310 may be made of a flexible material capable of maintaining a seal, such as plastic or rubber. The cap 310 may be plastic, or metal, or any other rigid or semi-rigid material. Using a pivot portion 340 of the cap 310, the cap 310 and seal 330 may be pivoted into position to form an air-tight seal on the drug reservoir 320. Such a device to cap the drug reservoir 320 may involve the seal 330 deforming or partially deforming to squeeze between the sides of the drug reservoir 320, thereby creating an airtight seal. Cap 310 may be manipulated to unseal drug reservoir 320 to remove and/or add liquid drug to drug reservoir 320. Cap 310 may then be maneuvered to reseal drug reservoir 320.

FIG. 4 illustrates another embodiment 400 of cap to seal a nebulizer, such as the nebulizers of FIGS. 1A-1D, or some other nebulizer. The embodiment of FIG. 4 may include a one-way valve such as valve 440. FIG. 4 illustrates an embodiment of a cap 450 with a "burp" valve 440. Such a valve 440 prevents a positive bias pressure from being generated in the drug reservoir 410 of the nebulizer to equalize with the external atmospheric pressure and allows the ambient pressure to be maintained. However, valve 440 does not allow air to move from the external environment to inside drug reservoir 410. Cap 450 may also include o-rings 420 to maintain a seal between the cap 450 and the drug reservoir 410. Further, flanges 430 may also form an additional airtight seal between cap 450 and the drug reservoir 410. Alternatively, flange 430 may not be airtight. It may be possible to pull cap 450 off of drug reservoir 410 to add and/or remove liquid drug. Cap 450 may then be reattached to drug reservoir 410.

Figure 5:
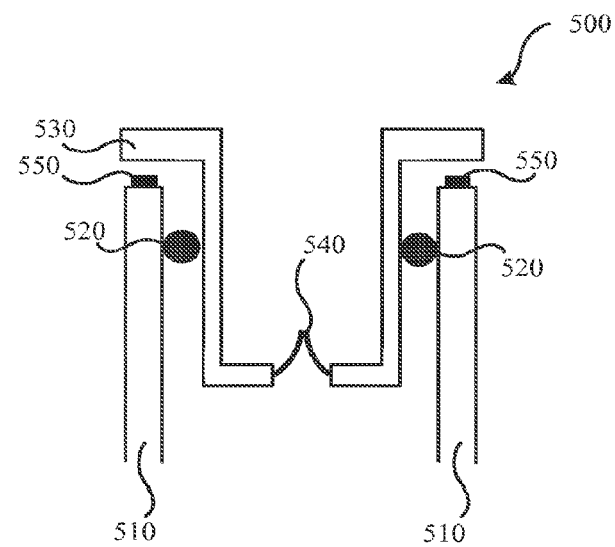
FIG. 5 illustrates a simplified embodiment of a cap that may seal a drug reservoir.

Embodiment 500 of FIG. 5 illustrates an additional way of sealing a drug reservoir of a nebulizer that may allow for the creation of a negative bias pressure within drug reservoir 510. Such a way of sealing a drug reservoir may be used in conjunction with the nebulizers of FIGS. 1A-1D, or some other nebulizer. Embodiment 500 may also include a one-way "burp" valve 540 to allow air to exit and the ambient pressure to be maintained, instead of creating a positive bias pressure within the drug reservoir 510. Valve 540 may prevent air from the external environment from entering drug reservoir 510. O-rings 520 may be used to form the seal between the cap 530 and the drug reservoir 510. Additional seals 550 may be present to create a seal between the drug reservoir 510 and the cap 530. In such an embodiment, the depth of the cap 530 may be varied to regulate the head space within the drug reservoir 510. For example, the greater the depth of cap 530, the smaller the amount of head space that will be present in drug reservoir 510. Additionally, it may be possible to remove cap 530 to add and/or remove liquid drug from drug reservoir 510. Cap 530 may then be reinserted to seal drug reservoir 510.

Figure 6A:
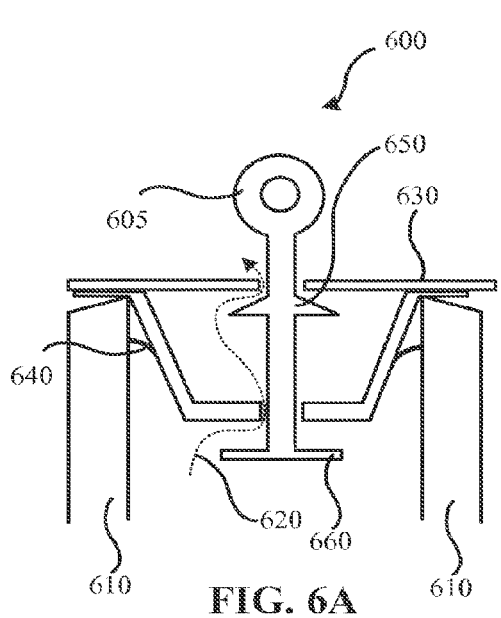
FIGS. 6A and 6B illustrate a simplified embodiment of a cap that may seal a drug reservoir.
Figure 6B:
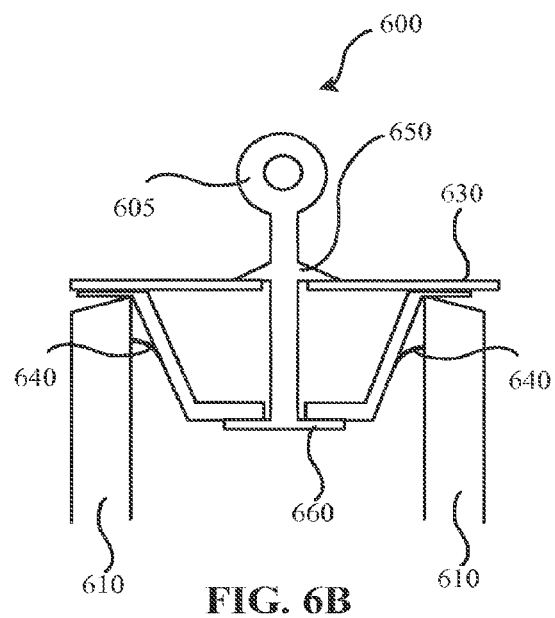

FIGS. 6A and 6B illustrate an embodiment 600 of a cap that may be used to create a sealed drug reservoir for a nebulizer, such as the nebulizers of FIGS. 1A-1D, or some other nebulizer. FIG. 6A illustrates the cap 630 prior to sealing with the drug reservoir 610. In such an embodiment, the cap may be placed on the drug reservoir 610 without a positive bias pressure developing because of an escape route for the air (thereby the ambient pressure being maintained), illustrated by dotted arrow 620. The cap 630 may use flange 640 to create a seal between the drug reservoir 610 and the edge of the cap 630. In some embodiments, an o-ring is used in place of flange 640. Cap 630 may contain plunger 605. The plunger may be attached to a unidirectional lock 650 and a stopper 660. The stopper may be capable of creating an airtight seal with the bottom of the cap 630 when the plunger 605 has been elevated. The unidirectional lock 650 may prevent the plunger 605 from being depressed once the unidirectional lock 650 has passed through an opening in the cap 630. The unidirectional lock 650 may be made of a flexible or semi-flexible material. The unidirectional lock 650 may also form an airtight seal with the cap 630. The cap 630 may be shaped to eliminate various amounts of head space within the drug reservoir 610. For example, the depth of cap 630 may be increased to eliminate an increased amount of head space from drug reservoir 610. Once cap 630 has been inserted, plunger 605 may be pulled to seal the cap 630 to the drug reservoir 610.

FIG. 6B illustrates cap 630 after the plunger 605 has been raised. A user may raise plunger 605 manually. The stopper 660 may have formed an airtight seal with the bottom of the cap 630. In this embodiment, the unidirectional lock 650 has passed though the cap 630, preventing the plunger 605 from descending and/or breaking the seal between the cap 630 and the drug reservoir 610. Additionally, unidirectional lock 650 may form an airtight seal with the top of cap 630. It may be possible to unseal cap 630 by pushing plunger 605 such that unidirectional lock 650 is forced back through the top of cap 630. Cap 630 may be removed to allow liquid drug to be added and/or removed from drug reservoir 610. In some embodiments, once unidirectional lock 650 has passed through cap 630, such as in FIG. 6B, it may not be possible to unseal cap 630 using plunger 605. However, it may still be possible to remove cap 630, add and/or remove additional liquid drug and reseal drug reservoir 610 using a new cap 630.

As those with skill in the art will realize, the embodiments of FIGS. 2-6 represent examples of possible embodiments of caps to seal a drug reservoir of a nebulizer. Other embodiments of caps may also be possible. Further, it may be possible to create a permanently capped reservoir. Such a permanently sealed reservoir may be formed from a single piece of material or may include a distinct cap permanently attached to the drug reservoir of the nebulizer. Such a permanently sealed drug reservoir may be used once and then disposed.

Such embodiments of nebulizers and caps, such as those described in FIGS. 1A-1D, and FIGS. 2-6 may allow for a drug reservoir of a nebulizer to be sealed using a method, such as method 700 of FIG. 7. At stage 710, a drug reservoir of a nebulizer may receive liquid, such as any of the previously described liquid drugs into a drug reservoir. At stage 720, this liquid may be stored in the drug reservoir until the liquid drug is either removed or aerosolized.

At stage 730, the liquid reservoir may be sealed. The process of such sealing may allow for air to escape from the liquid reservoir to prevent a positive bias pressure within the drug reservoir from developing, and thus maintain the ambient pressure within the drug reservoir. Once sealed, if any positive pressure within the liquid reservoir is present it may still be allowed to escape, however air from the external environment is not permitted to enter the drug reservoir. The ambient pressure may then be maintained within the drug reservoir until liquid drug is dispensed from the drug reservoir.

At stage 740, liquid drug may be discharged from the drug reservoir to the aperture plate of the nebulizer. Because the drug reservoir is sealed, air may not enter the drug reservoir as the liquid drug is discharged.

At stage 750, the liquid drug may be aerosolized by the aperture plate. The aperture plate may be vibrating. As liquid drug contacts the aperture plate and moves through openings in the aperture plate, the liquid drug may become atomized into small airborne particles. Such airborne particles may be suitable for inhalation by a person.

At stage 760, as liquid is discharged from the drug reservoir and is aerosolized by the aperture plate, a negative bias pressure may develop within the drug reservoir. The negative bias pressure may develop because neither air nor anything else is permitted to enter the drug reservoir to take the place of the liquid drug as it is being discharged.

FIG. 8 illustrates another embodiment 800 of a method that allows for a drug reservoir of a nebulizer to be sealed and a negative bias pressure to form within the drug reservoir. Further, embodiment 800 allows for additional liquid drug to be added after the drug reservoir has been sealed. Such embodiments of nebulizers and caps, such as those described in FIGS. 1A-1D, and FIGS. 2-6 may allow for embodiment 800 to be performed.

At stage 810, a drug reservoir of a nebulizer may receive liquid, such as any of the previously described liquid drugs into a drug reservoir. At stage 820, this liquid may be stored in the drug reservoir until the liquid drug is either removed or aerosolized.

At stage 830, the liquid reservoir may be sealed. The process of such sealing may allow for air to escape from the liquid reservoir to prevent a positive bias pressure within the drug reservoir from developing. Once sealed, any positive pressure within the liquid reservoir may still be allowed to escape, however air from the external environment is not permitted to enter the drug reservoir.

At stage 840, liquid drug may be discharged from the drug reservoir to the aperture plate of the nebulizer. Because the drug reservoir is sealed, air may not enter the drug reservoir as the liquid drug is discharged.

At stage 845, the nebulizer may receive a control signal from a control unit, such as control unit 152 of FIG. 1B. The control signal may be at a frequency and a voltage. The frequency and magnitude of the voltage may determine the rate and amplitude of the vibration of the aperture plate of the nebulizer. The rate and amplitude of the aperture plate's vibration may determine the amount of liquid drug aerosolized and the size of the liquid drug droplets that are created by the aperture plate.

At stage 850, the liquid drug may be aerosolized by the aperture plate based on the control signal received at stage 845. As liquid drug contacts the aperture plate and moves through openings in the aperture plate, the liquid drug may become atomized into small airborne particles. Such airborne particles may be suitable for inhalation by a person.

At stage 860, as liquid is discharged from the drug reservoir and is aerosolized by the aperture plate, a negative bias pressure may develop within the drug reservoir. The negative bias pressure may develop because neither air nor anything else is permitted to enter the drug reservoir to take the place of the liquid drug as it is being discharged.

At stage 865, after some amount of liquid drug has been aerosolized and a negative bias pressure has been created within the drug reservoir, it may be determined whether additional liquid drug is to be added to the drug reservoir. Additionally, it may be determined whether liquid drug will be removed from the drug reservoir. If no, the method may end at stage 870. The negative bias pressure created at stage 860 may remain until some future time.

However, if at stage 865 additional liquid drug is to be added (or removed) from the drug reservoir, the drug reservoir cap may be removed at stage 875. This may involve removing the entire cap. For example, referring to FIG. 3, cap 310 may be entirely removed such that drug reservoir 320 may be accessed. This may involve manipulating only a portion of the cap. In some embodiments, only a portion of the cap may be removed. For example, referring to FIG. 2, screw down insert 210 may be unscrewed (or otherwise removed) while the remainder of cap 230 remains attached to drug reservoir 220.

At stage 880, additional liquid may be received in the drug reservoir. This may represent the same or different liquid drug than what was aerosolized at stage 850. Drug reservoir may also be cleaned, especially if a different liquid drug is to be aerosolized. This additional liquid drug may be stored by the drug reservoir at block 890. The method may then return to block 830, where the drug reservoir may be resealed using the same cap or a different cap. The method may then continue until no additional liquid drug is to be aerosolized.

While a wide variety of drugs, liquids, liquid drugs, and drugs dissolved in liquid may be aerosolized, the following provides extensive examples of what may be aerosolized. Additional examples are provided in U.S. application Ser. No. 12/341,780, the entire disclosure of which is incorporated herein for all purposes. Nearly any anti-gram-negative, anti-gram-positive antibiotic, or combinations thereof may be used. Additionally, antibiotics may comprise those having broad spectrum effectiveness, or mixed spectrum effectiveness. Antifungals, such as polyene materials, in particular, amphotericin B are also suitable for use herein. Examples of anti-gram-negative antibiotics or salts thereof include, but are not limited to, aminoglycosides or salts thereof. Examples of aminoglycosides or salts thereof include gentamicin, amikacin, kanamycin, streptomycin, neomycin, netilmicin, paramecin, tobramycin, salts thereof, and combinations thereof. For instance, gentamicin sulfate is the sulfate salt, or a mixture of such salts, of the antibiotic substances produced by the growth of *Micromonospora purpurea*. Gentamicin sulfate, USP, may be obtained from Fujian Fukang Pharmaceutical Co., LTD, Fuzhou, China. Amikacin is typically supplied as a sulfate salt, and can be obtained, for example, from Bristol-Myers Squibb. Amikacin may include related substances such as kanamicin.

Examples of anti-gram-positive antibiotics or salts thereof include, but are not limited to, macrolides or salts thereof. Examples of macrolides or salts thereof include, but are not limited to erythromycin, clarithromycin, azithromycin, salts thereof, and combinations thereof. For instance, vancomycin hydrochloride is a hydrochloride salt of vancomycin, an antibiotic produced by certain strains of *Amycolatopsis orientalis*, previously designated *Streptomyces orientalis*. Vancomycin hydrochloride is a mixture of related substances consisting principally of the monohydrochloride of vancomycin B. Like all glycopeptide antibiotics, vancomycin hydrochloride contains a central core heptapeptide. Vancomycin hydrochloride, USP, may be obtained from Alpharma, Copenhagen, Denmark.

In some embodiments, the composition comprises an antibiotic and one or more additional active agents. The additional active agent described herein includes an agent, drug, or compound, which provides some pharmacologic, often beneficial, effect. This includes foods, food supplements, nutrients, drugs, vaccines, vitamins, and other beneficial agents. As used herein, the terms further include any physiologically or pharmacologically active substance that produces a localized or systemic effect in a patient. An active agent for incorporation in the pharmaceutical formulation described herein may be an inorganic or an organic compound, including, without limitation, drugs which act on: the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system, and the central nervous system.

Examples of additional active agents include, but are not limited to, anti-inflammatory agents, bronchodilators, and combinations thereof.

Examples of bronchodilators include, but are not limited to, β-agonists, anti-muscarinic agents, steroids, and combinations thereof. For instance, the bronchodilator may comprise albuterol, such as albuterol sulfate.

Active agents may comprise, for example, hypnotics and sedatives, psychic energizers, tranquilizers, respiratory drugs, anticonvulsants, muscle relaxants, antiparkinson agents (dopamine antagonists), analgesics, anti-inflammatories, antianxiety drugs (anxiolytics), appetite suppressants, antimigraine agents, muscle contractants, additional anti-infectives (antivirals, antifungals, vaccines) antiarthritics, antimalarials, antiemetics, anepileptics, cytokines, growth factors, anti-cancer agents, antithrombotic agents, antihypertensives, cardiovascular drugs, antiarrhythmics, antioxidants, anti-asthma agents, hormonal agents including contraceptives, sympathomimetics, diuretics, lipid regulating agents, antiandrogenic agents, antiparasitics, anticoagulants, neoplastics, antineoplastics, hypoglycemics, nutritional agents and supplements, growth supplements, antienteritis agents, vaccines, antibodies, diagnostic agents, and contrasting agents. The active agent, when administered by inhalation, may act locally or systemically.

The active agent may fall into one of a number of structural classes, including but not limited to small molecules, peptides, polypeptides, proteins, polysaccharides, steroids, proteins capable of eliciting physiological effects, nucleotides, oligonucleotides, polynucleotides, fats, electrolytes, and the like.

Examples of active agents suitable for use in this invention include but are not limited to one or more of calcitonin, amphotericin B, erythropoietin (EPO), Factor VIII, Factor IX, ceredase, cerezyme, cyclosporin, granulocyte colony stimulating factor (GCSF), thrombopoietin (TPO), alpha-1 proteinase inhibitor, elcatonin, granulocyte macrophage colony stimulating factor (GMCSF), growth hormone, human growth hormone (HGH), growth hormone releasing hormone (GHRH), heparin, low molecular weight heparin (LMWH), interferon alpha, interferon beta, interferon gamma, interleukin-1 receptor, interleukin-2, interleukin-1 receptor antagonist, interleukin-3, interleukin-4, interleukin-6, luteinizing hormone releasing hormone (LHRH), factor IX, insulin, pro-insulin, insulin analogues (e.g., mono-acylated insulin as described in U.S. Pat. No. 5,922,675, which is incorporated herein by reference in its entirety), amylin, C-peptide, somatostatin, somatostatin analogs including octreotide, vasopressin, follicle stimulating hormone (FSH), insulin-like growth factor (IGF), insulintropin, macrophage colony stimulating factor (M-CSF), nerve growth factor (NGF), tissue growth factors, keratinocyte growth factor (KGF), glial growth factor (GGF), tumor necrosis factor (TNF), endothelial growth factors, parathyroid hormone (PTH), glucagon-like peptide thymosin alpha 1, IIb/IIIa inhibitor, alpha-1 antitrypsin, phosphodiesterase (PDE) compounds, VLA-4 inhibitors, bisphosphonates, respiratory syncytial virus antibody, cystic fibrosis transmembrane regulator (CFTR) gene, deoxyreibonuclease (Dnase), bactericidal/permeability increasing protein (BPI), anti-CMV antibody, 1 3-cis retinoic acid, oleandomycin, troleandomycin, roxithromycin, clarithromycin, davercin, azithromycin, flurithromycin, dirithromycin, josamycin, spiromycin, midecamycin, leucomycin, miocamycin, rokitamycin, andazithromycin, and swinolide A; fluoroquinolones such as ciprofloxacin, ofloxacin, levofloxacin, trovafloxacin, alatrofloxacin, moxifloxicin, norfloxacin, enoxacin, grepafloxacin, gatifloxacin, lomefloxacin, sparfloxacin, temafloxacin, pefloxacin, amifloxacin, fleroxacin, tosufloxacin, prulifloxacin, irloxacin, pazufloxacin, clinafloxacin, and sitafloxacin, teicoplanin, rampolanin, mideplanin, colistin, daptomycin, gramicidin, colistimethate, polymixins such as polymixin B, capreomycin, bacitracin, penems; penicillins including penicllinase-sensitive agents like penicillin G, penicillin V, penicillinase-resistant agents like methicillin, oxacillin, cloxacillin, dicloxacillin, floxacillin, nafcillin; gram negative microorganism active agents like ampicillin, amoxicillin, and hetacillin, cillin, and galampicillin; antipseudomonal penicillins like carbenicillin, ticarcillin, azlocillin, mezlocillin, and piperacillin; cephalosporins like cefpodoxime, cefprozil, ceftbuten, ceftizoxime, ceftriaxone, cephalothin, cephapirin, cephalexin, cephradrine, cefoxitin, cefamandole, cefazolin, cephaloridine, cefaclor, cefadroxil, cephaloglycin, cefuroxime, ceforanide, cefotaxime, cefatrizine, cephacetrile, cefepime, cefixime, cefonicid, cefoperazone, cefotetan, cefinetazole, ceftazidime, loracarbef, and moxalactam, monobactams like aztreonam; and carbapenems such as imipenem, meropenem, pentamidine isethiouate, lidocaine, metaproterenol sulfate, beclomethasone diprepionate, triamcinolone acetamide, budesonide acetonide, fluticasone, ipratropium bromide, flunisolide, cromolyn sodium, ergotamine tartrate and where applicable, analogues, agonists, antagonists, inhibitors, and pharmaceutically acceptable salt forms of the above. In reference to peptides and proteins, the invention is intended to encompass synthetic, native, glycosylated, unglycosylated, pegylated forms, and biologically active fragments, derivatives, and analogs thereof.

Active agents for use in the invention further include nucleic acids, as bare nucleic acid molecules, vectors, associated viral particles, plasmid DNA or RNA or other nucleic acid constructions of a type suitable for transfection or transformation of cells, i.e., suitable for gene therapy including antisense. Further, an active agent may comprise live attenuated or killed viruses suitable for use as vaccines. Other useful drugs include those listed within the Physician's Desk Reference (most recent edition), which is incorporated herein by reference in its entirety.

The amount of antibiotic or other active agent in the pharmaceutical formulation will be that amount necessary to deliver a therapeutically or prophylactically effective amount of the active agent per unit dose to achieve the desired result. In practice, this will vary widely depending upon the particular agent, its activity, the severity of the condition to be treated, the patient population, dosing requirements, and the desired therapeutic effect. The composition will generally contain anywhere from about 1 wt % to about 99 wt %, such as from about 2 wt % to about 95 wt %, or from about 5 wt % to 85 wt %, of the active agent, and will also depend upon the relative amounts of additives contained in the composition. The compositions of the invention are particularly useful for active agents that are delivered in doses of from 0.001 mg/day to 100 mg/day, such as in doses from 0.01 mg/day to 75 mg/day, or in doses from 0.10 mg/day to 50 mg/day. It is to be understood that more than one active agent may be incorporated into the formulations described herein and that the use of the term "agent" in no way excludes the use of two or more such agents.

Generally, the compositions are free of excessive excipients. In one or more embodiments, the aqueous composition consists essentially of the anti-gram-negative antibiotic, such as amikacin, or gentamicin or both, and/or salts thereof and water.

Further, in one or more embodiments, the aqueous composition is preservative-free. In this regard, the aqueous composition may be methylparaben-free and/or propylparaben-free. Still further, the aqueous composition may be saline-free.

In one or more embodiments, the compositions comprise an anti-infective and an excipient. The compositions may comprise a pharmaceutically acceptable excipient or carrier which may be taken into the lungs with no significant adverse toxicological effects to the subject, and particularly to the lungs of the subject. In addition to the active agent, a pharmaceutical formulation may optionally include one or more pharmaceutical excipients which are suitable for pulmonary administration. These excipients, if present, are generally present in the composition in amounts sufficient to perform their intended function, such as stability, surface modification, enhancing effectiveness or delivery of the composition or the like. Thus if present, excipient may range from about 0.01 wt % to about 95 wt %, such as from about 0.5 wt % to about 80 wt %, from about 1 wt % to about 60 wt %. Preferably, such excipients will, in part, serve to further improve the features of the active agent composition, for example by providing more efficient and reproducible delivery of the active agent and/or facilitating manufacturing. One or more excipients may also be provided to serve as bulking agents when it is desired to reduce the concentration of active agent in the formulation.

For instance, the compositions may include one or more osmolality adjuster, such as sodium chloride. For instance, sodium chloride may be added to solutions of vancomycin hydrochloride to adjust the osmolality of the solution. In one or more embodiments, an aqueous composition consists essentially of the anti-gram-positive antibiotic, such as vancomycin hydrochloride, the osmolality adjuster, and water.

Pharmaceutical excipients and additives useful in the present pharmaceutical formulation include but are not limited to amino acids, peptides, proteins, non-biological polymers, biological polymers, carbohydrates, such as sugars, derivatized sugars such as alditols, aldonic acids, esterified sugars, and sugar polymers, which may be present singly or in combination.

Exemplary protein excipients include albumins such as human serum albumin (HSA), recombinant human albumin (rHA), gelatin, casein, hemoglobin, and the like. Suitable amino acids (outside of the dileucyl-peptides of the invention), which may also function in a buffering capacity, include alanine, glycine, arginine, betaine, histidine, glutamic acid, aspartic acid, cysteine, lysine, leucine, isoleucine, valine, methionine, phenylalanine, aspartame, tyrosine, tryptophan, and the like. Preferred are amino acids and polypeptides that function as dispersing agents. Amino acids falling into this category include hydrophobic amino acids such as leucine, valine, isoleucine, tryptophan, alanine, methionine, phenylalanine, tyrosine, histidine, and proline.

Carbohydrate excipients suitable for use in the invention include, for example, monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), pyranosyl sorbitol, myoinositol and the like.

The pharmaceutical formulation may also comprise a buffer or a pH adjusting agent, typically a salt prepared from an organic acid or base. Representative buffers comprise organic acid salts of citric acid, ascorbic acid, gluconic acid, carbonic acid, tartaric acid, succinic acid, acetic acid, or phthalic acid, Tris, tromethamine hydrochloride, or phosphate buffers.

The pharmaceutical formulation may also include polymeric excipients/additives, e.g., polyvinylpyrrolidones, celluloses and derivatized celluloses such as hydroxymethylcellulose, hydroxyethylcellulose, and hydroxypropylmethylcellulose, Ficolls (a polymeric sugar), hydroxyethylstarch, dextrates (e.g., cyclodextrins, such as 2-hydroxypropyl-.beta.-cyclodextrin and sulfobutylether-.beta.-cyclodextrin), polyethylene glycols, and pectin.

The pharmaceutical formulation may further include flavoring agents, taste-masking agents, inorganic salts (for example sodium chloride), antimicrobial agents (for example benzalkonium chloride), sweeteners, antioxidants, antistatic agents, surfactants (for example polysorbates such as "TWEEN 20" and "TWEEN 80"), sorbitan esters, lipids (for example phospholipids such as lecithin and other phosphatidylcholines, phosphatidylethanolamines), fatty acids and fatty esters, steroids (for example cholesterol), and chelating agents (for example EDTA, zinc and other such suitable cations). Other pharmaceutical excipients and/or additives suitable for use in the compositions according to the invention are listed in "Remington: The Science & Practice of Pharmacy", 19.sup.th ed., Williams & Williams, (1995), and in the "Physician's Desk Reference", 52.sup.nd ed., Medical Economics, Montvale, N.J. (1998), both of which are incorporated herein by reference in their entireties.

It should be noted that the methods, systems, and devices discussed above are intended merely to be examples. It must be stressed that various embodiments may omit, substitute, or add various procedures or components as appropriate. For instance, it should be appreciated that, in alternative embodiments, the methods may be performed in an order different from that described, and that various steps may be added, omitted, or combined. Also, features described with respect to certain embodiments may be combined in various other embodiments. Different aspects and elements of the embodiments may be combined in a similar manner. Also, it should be emphasized that technology evolves and, thus, many of the elements are examples and should not be interpreted to limit the scope of the invention.

Specific details are given in the description to provide a thorough understanding of the embodiments. However, it will be understood by one of ordinary skill in the art that the embodiments may be practiced without these specific details. For example, well-known processes, algorithms, structures, and techniques have been shown without unnecessary detail in order to avoid obscuring the embodiments. This description provides example embodiments only, and is not intended to limit the scope, applicability, or configuration of the invention. Rather, the preceding description of the embodiments will provide those skilled in the art with an enabling description for implementing embodiments of the invention. Various changes may be made in the function and arrangement of elements without departing from the spirit and scope of the invention.

Further, the preceding description generally details aerosolizing liquid drugs. However, it should be understood that liquids besides liquid drugs may be aerosolized using similar devices and methods.

Also, it is noted that the embodiments may be described as a process which is depicted as a flow diagram or block diagram. Although each may describe the operations as a sequential process, many of the operations can be performed in parallel or concurrently. In addition, the order of the operations may be rearranged. A process may have additional steps not included in the figure.

What is claimed is:

1. A nebulizer system comprising:
an aerosol generator comprising an aperture plate, wherein the aperture plate is configured to be vibrated to aerosolize a liquid;
a liquid reservoir that is configured to store the liquid such that a headspace is present within the liquid reservoir and discharges the liquid to the aerosol generator;
a sealing structure; and
a cap for use in sealing the liquid reservoir and decreasing a volume of the headspace of the liquid reservoir, wherein:
the sealing structure forms a seal between the liquid reservoir and the cap;
the cap comprises a passageway that permits air to pass from the headspace of the liquid reservoir into an external environment, such that air passes through the passageway from the liquid reservoir into the external environment while the seal created between the liquid reservoir and the cap is present;

the cap maintains an ambient pressure while the liquid reservoir is being sealed by allowing air to exit the headspace through the passageway;

following the liquid reservoir being sealed with the cap, the cap maintains ambient pressure in the sealed liquid reservoir until a portion of the liquid is dispensed; and the cap permits a negative pressure within the liquid reservoir to develop as liquid is discharged from the liquid reservoir after the liquid reservoir has been sealed using the cap.

2. The nebulizer system of claim 1, wherein the cap further comprises a first set of threads that are configured to screw down into a second set of threads.

3. The nebulizer system of claim 2, wherein the passageway of the cap comprises a first opening and a second opening, wherein the second opening is located lower on the cap than the first opening.

4. The nebulizer system of claim 2, wherein the passageway is configured to maintain the ambient pressure in the liquid reservoir as the first set of threads is screwed into the second set of threads and the headspace of the liquid reservoir is decreased.

5. The nebulizer system of claim 4, wherein the first set of threads being screwed down into the second set of threads prevents the passageway from permitting air to exchange between the headspace of the liquid reservoir and the external environment.

6. The nebulizer system of claim 1, further comprising:
a driver unit that generates and outputs a control signal having a voltage and a frequency.

7. The nebulizer system of claim 6, wherein:
the aerosol generator is configured to receive the control signal from the driver unit; and
the aerosol generator is further configured to use the control signal from the driver unit to vibrate the aperture plate to aerosolize liquid.

8. A liquid storage device for use with a nebulizer, the liquid storage device comprising:
a liquid reservoir configured to hold liquid such that a headspace is present within the liquid reservoir above the liquid; and
the liquid reservoir discharges the liquid to an aperture plate of the nebulizer;
a sealing ring; and
a cap configured for sealing the liquid reservoir, wherein:
the sealing ring forms a seal between the liquid reservoir and the cap;
the cap decreases the headspace when sealed on the liquid reservoir;
the cap comprises a passageway that permits air to pass from the headspace of the liquid reservoir into an ambient environment, such that air passes through the passageway from the liquid reservoir into the external environment while the seal created between the liquid reservoir and the cap is present;
the cap causes an ambient pressure to be maintained while the liquid reservoir is being sealed by allowing air to exit the headspace through the passageway into the ambient environment;
following the liquid reservoir being sealed with the cap, the ambient pressure is maintained in the liquid reservoir until liquid is dispensed to the aperture plate; and the cap permits a negative pressure within the liquid reservoir to develop as liquid is discharged from the liquid reservoir to the aperture plate of the nebulizer after the liquid reservoir has been sealed using the cap, the passageway being inhibited from permitting an entrance of air from the ambient environment into the headspace.

9. The liquid storage device for the nebulizer of claim 8, wherein the cap further comprises threads for screwing the cap down.

10. The liquid storage device for the nebulizer of claim 9, wherein the passageway of the cap comprises a first opening and a second opening, wherein the second opening is located lower on the cap than the first opening.

11. The liquid storage device for the nebulizer of claim 9, wherein the passageway maintains the ambient pressure in the liquid reservoir as the threads are used for screwing the cap down by permitting an exit of air from the headspace into the ambient environment.

12. The liquid storage device for the nebulizer of claim 11, wherein the cap being screwed down a distance via the threads inhibits the passageway from permitting an exchange of air between the headspace of the liquid reservoir and the ambient environment.

13. The liquid storage device for the nebulizer of claim 8, wherein the liquid is a drug.

14. A method for creating a negative pressure within a sealed reservoir, the method comprising:
providing an aerosol generator, the aerosol generator comprising an aperture plate, the aperture plate having a liquid side and an air side;
storing a liquid in a liquid reservoir such that the liquid is in fluid communication with the liquid side of the aperture plate and such that a headspace is present within the liquid reservoir;
providing a cap for the liquid reservoir, the cap comprising a passageway that permits air to exit the headspace during sealing but does not permit air to exit the headspace following sealing;
sealing the liquid reservoir by attaching the cap to the liquid reservoir such that the cap fills a portion of the headspace of the liquid reservoir and a seal is formed between the liquid reservoir and the cap, wherein:
an ambient pressure is maintained while the liquid reservoir is being sealed by air exiting the headspace via the passageway while the seal between the liquid reservoir and the cap is present; and
the ambient pressure is maintained in the sealed liquid reservoir until a portion of the liquid is dispensed; and
vibrating the aperture plate to dispense the portion of the liquid from the air side of the aperture plate, wherein:
dispensing the portion of the liquid decreases the amount of the liquid in the sealed reservoir; and
decreasing the amount of liquid in the sealed reservoir creates a negative pressure within the headspace as compared to atmospheric pressure.

15. The method of claim 14, wherein the cap is configured to screw into threads; and the method further comprises:
screwing the cap, wherein the passageway allows the ambient pressure to be maintained in the liquid reservoir as the portion of the cap is screwed.

16. The method of claim 15, wherein screwing the cap decreases the headspace within the liquid reservoir.

17. The method of claim 15, wherein at least a portion of the cap that fills the headspace cannot be unscrewed.

18. The method of claim 14, further comprising receiving, by the aerosol generator, a control signal from a driver unit, wherein the control signal from the driver unit is used to vibrate the aperture plate to dispense the portion of the liquid.

19. The method of claim 14, wherein the liquid is a drug and the liquid reservoir is a liquid drug reservoir.

* * * * *